United States Patent [19]

LaSalle et al.

[11] Patent Number: 5,713,410
[45] Date of Patent: Feb. 3, 1998

[54] BONE PROSTHESES WITH DIRECT CAST MACROTEXTURED SURFACE REGIONS AND METHOD FOR MANUFACTURING THE SAME

[75] Inventors: David L. LaSalle, Woonsocket, R.I.; Timothy M. Flynn, Norton, Mass.; Salvatore Caldarise, Hanson, Mass.; Richard P. Manginelli, Milton, Mass.

[73] Assignee: Johnson & Johnson Professional, Inc., Raynham, Mass.

[21] Appl. No.: 457,691

[22] Filed: Jun. 1, 1995

Related U.S. Application Data

[62] Division of Ser. No. 198,607, Feb. 18, 1994, Pat. No. 5,665,118.

[51] Int. Cl.$^6$ ........................................... B22C 7/02
[52] U.S. Cl. .................. 164/516; 164/34; 164/45; 164/4.1
[58] Field of Search .................. 164/34, 35, 45, 164/4.1, 516; 264/308, 401, DIG. 51; 156/275.5

[56] References Cited

U.S. PATENT DOCUMENTS

| | | | |
|---|---|---|---|
| 4,330,891 | 5/1982 | Branemark et al. | 3/1 |
| 4,355,428 | 10/1982 | Deloison et al. | 3/1.91 |
| 4,479,271 | 10/1984 | Bolesky et al. | 3/1.911 |
| 4,608,052 | 8/1986 | Van Kampen et al. | 623/22 |
| 4,778,469 | 10/1988 | Lin et al. | 623/16 |
| 4,828,563 | 5/1989 | Müller-Lierheim | 623/16 |
| 4,863,474 | 9/1989 | Brown et al. | 623/16 |
| 4,865,608 | 9/1989 | Brooker, Jr. | 623/23 |
| 4,929,402 | 5/1990 | Hull | 264/308 |
| 5,042,560 | 8/1991 | Ahlers | 164/34 |
| 5,108,435 | 4/1992 | Gustavson et al. | 623/16 |
| 5,178,201 | 1/1993 | Ahlers | 164/34 |
| 5,204,055 | 4/1993 | Sachs et al. | 419/2 |
| 5,207,709 | 5/1993 | Picha | 623/11 |
| 5,222,983 | 6/1993 | Schmitz et al. | 623/16 |
| 5,236,457 | 8/1993 | Devanathan | 623/16 |
| 5,524,695 | 6/1996 | Schwartz | 164/34 |

FOREIGN PATENT DOCUMENTS

| | | |
|---|---|---|
| A-0 566 427 | 10/1993 | European Pat. Off. |
| A-41 02 256 | 7/1992 | Germany. |
| WO 92/21302 | 12/1992 | WIPO. |
| WO 93/07835 | 4/1993 | WIPO. |
| WO-A-93 16865 | 9/1993 | WIPO. |

*Primary Examiner*—Kuang Y. Lin
*Attorney, Agent, or Firm*—Nutter, McClennen & Fish, LLP

[57] ABSTRACT

An implantable article having on at least a portion of its exterior surface an integral, as-cast macrotextured surface having pores with undercut edge profiles is provided. The integral, as-cast macrotextured surface is able to be formed on the implantable articles by a modified casting process. As part of a casting process, positive models of the articles to be cast, or parts thereof, are formed by stereolithographic techniques. Cavities or molds, representing negative images of the articles to be cast, are then formed by encasing one or more models in a refractory material. The positive models are then extracted by heating and thus melting the material from which they are made. Thereafter, molten casting material can be poured into the resulting mold to obtain the implantable articles.

8 Claims, 5 Drawing Sheets

(DETAIL "A")

BONE PROSTHESES WITH DIRECT CAST MACROTEXTURED SURFACE REGIONS AND METHOD FOR MANUFACTURING THE SAME

This is a divisional of application Ser. No. 08/198,607 filed on Feb. 18, 1994, now U.S. Pat. No. 5,665,118.

This application is related to U.S. patent application Ser. No. 08/198,874, filed concurrently herewith and entitled "IMPLANTABLE ARTICLES WITH AS-CAST MACRO-TEXTURED SURFACE REGIONS AND METHOD OF MANUFACTURING THE SAME", which is hereby incorporated by reference.

BACKGROUND OF THE INVENTION

The invention relates to implantable articles and methods for manufacturing such articles. More particularly, the invention relates to bone prostheses and investment casting processes for manufacturing the same.

There are known to exist many designs for and methods for manufacturing implantable articles, such as bone prostheses. Such bone prostheses include components of artificial joints, such as elbows, hips, knees, and shoulders. An important consideration in the design and manufacture of virtually any implantable bone prosthesis is that the prosthesis have adequate fixation when implanted within the body.

Early designs of implantable articles relied upon the use of cements such as polymethylmethacrylate to anchor the implant. The use of such cements can have some advantages, such as providing an immediate and secure fixation that does not develop free play and lead to erosion of the joining bone faces post-operatively. However, the current trend is to use these cements to a lesser extent because they tend to lose their adhesive properties over time and because they can contribute to wear debris within a replaced joint.

Recently, implantable bone prostheses have been designed such that they encourage the growth of hard tissue (i.e., bone) around the implant. Bone ingrowth usually occurs and growth is promoted where the surface of an implantable bone prosthesis is irregular or textured. The interaction of newly formed hard tissue in and around the textured surface of the implantable bone prosthesis has been established to provide good fixation of the prosthesis within the body. Greater bone fixation can usually be achieved where bone contacting surfaces of an implantable bone prosthesis are more porous or irregular.

Porous or irregular surfaces can be provided in implantable articles by a variety of techniques. In some instances irregular patterns or surface porosity is formed in an implantable bone prosthesis by embossing, chemical etching, milling or machining. One drawback to using such common techniques is the significant amount of post-processing time required. The post-processing operations lead to delays in obtaining the finished product and also significantly increase the cost of manufacturing the device. These post-processing operations can also degrade the mechanical properties of the device.

Textured surfaces are also applied to implantable bone prostheses by joining one or more separate surface plate inserts to an exterior surface of the prosthesis to provide separate porous surfaces or pore-forming surfaces. Separate pore-forming surfaces can be joined to or formed on an implantable bone prosthesis by sintering small metal particles or powders to a surface of the prosthesis in a random pattern. Wire-based pads or grids can also be fused to implantable bone prostheses to provide a texture or surface relief features. A drawback of such techniques is that the components added to form the textured surface can become dislodged from the prosthesis. Dislodgment of these components compromises the fixation mechanics of the implant and can also contribute to wear debris. Further, the sintering step required to fuse texture-forming components to bone prostheses is a high-temperature post-processing step that could impart mechanical weaknesses to the prosthesis, distort the dimensions of the prosthesis, and/or alter the properties of the materials from which the prosthesis is made.

Optimal bone fixation is believed to occur with implants that have more complex and irregular surfaces on a rather small dimensional scale, which provides a larger bone-contacting surface area with some depth of texture. Apparently, hard tissue (i.e., bone) is able to infiltrate small pores and passages that form the textured surface, thus providing firm interlock between the implant and the bone. It is also believed that the best textured surfaces for implantable bone prosthesis are those in which the porous surface is integral with the prosthesis, as opposed to porous surfaces that are separately fused to the prosthesis by post-processing operations.

An ideal textured surface would be one in which the macrotextured, porous region of an as-cast article includes pores with undercut edge profiles. Unfortunately, available technology has not previously enabled the manufacture of implantable articles with such macrotextured, porous surfaces.

Implantable articles such as bone prostheses are often made by an investment casting process. Investment casting first requires the manufacture of a solid model of the article to be cast. The solid model is often made from a meltable casting wax through a molding operation such as injection molding. Once the solid model is made, one or more of the solid models are fixed to a wax tree and the wax tree, together with the attached solid models, is encased in a binder material to form a shell. This is done by repeatedly dipping the assembly in a ceramic slurry coating and drying the coating between dips, to form a shell. After drying, the shell is heated to a temperature sufficient to melt and extract the casting wax from within the shell. Molten metal is then pored into the shell where it fills the cavities once occupied by the solid models, thereby forming east articles corresponding to the shape of the hollow regions left by the lost wax.

Although it is known to be useful to form implantable bone prostheses having as-cast macroporous textures, it is difficult to do so using the traditional investment casting techniques described above. The preparation of solid models by injection molding techniques is a serious limitation of such a process. It is difficult, if not impossible, to incorporate any suitable macrotextured surface into a solid model to be formed by an injection molding process because release of the model from the mold is likely to destroy the model. If the model has undercut surface features, it cannot be separated from the mold without breaking the model, and/or the mold.

Accordingly, there is a need for bone prostheses having improved textured surface characteristics that enhance the fixation mechanics of the implantable prostheses to hard tissue within the body. There is also a need for improved methods of manufacturing prostheses having such characteristics.

It is thus an object of the invention to provide implantable articles such as bone prostheses having surface characteristics that promote hard tissue ingrowth and improved fixation within the body. It is also an object of the invention to provide implantable bone prostheses having exterior, bone contacting surfaces that include an as-cast, macrotextured region. Another object of the invention is to provide casting techniques that enable the manufacture of implantable bone prostheses having as-cast macrotextured, porous surfaces. A further object of the invention is to provide casting techniques that facilitate the manufacture of implantable bone prostheses with as-cast macrotextured surfaces designed to take advantage of optimum fixation mechanics for a given prosthesis. These and other objects will be apparent from the description that follows.

SUMMARY OF THE INVENTION

The present invention provides implantable bone prostheses, such as those that are useful in forming artificial joints, that have improved fixation mechanics. A bone prosthesis manufactured according to the invention has an outer, bone-engaging surface, at least a portion of which has a macrotextured, porous surface. Preferably, the macrotextured, porous surface is integral with the prostheses and includes pores with: undercut edge profiles. The macrotextured surface is an as-cast surface.

The undercut edge profiles of pores provided by the present invention are believed to provide optimal fixation mechanics for the implantable articles on which they are formed. These macrotextured, porous surfaces provide increased surface area and permit substantial bone ingrowth that contributes a firm interlock between the implantable article and hard tissue within the body. The pores present in the macrotextured surface typically have diameters in the range of about 150 to 600 micrometers. Further, the implantable articles have a porosity in the range of about 30 to 60 percent.

The implantable articles of the invention preferably are formed from casting processes in combination with stereolithographic techniques. Solid, heat destructible models of the implantable articles are prepared by a stereolithography process. These heat destructible positive models of the article prepared by the stereolithography process are 3-dimensional objects that include exterior surfaces having a macrotextured, porous region. The macrotextured surface is characterized by pores that have undercut edge profiles.

One or more positive models can then be assembled on a runner system to form a cluster assembly. A shell of one or more coatings of a refractory binder material is then formed around the cluster assembly to yield an investment assembly. The positive models are recovered or removed from the investment assembly by heating the investment assembly to a temperature sufficient to melt or destroy the positive models and to extract the material from which they are made, leaving a shell having one or more cavities that form negatives of the articles to be cast. The shell is then filled with a molten casting material, such as a metal or metal alloy, such that the molten casting material fills the cavities in the shell to form, upon cooling, solid implantable articles. The formed implantable articles are characterized by at least a portion of their exterior surfaces being a macrotextured, porous surface that includes pores with undercut edge profiles.

DETAILED DESCRIPTION OF THE INVENTION

The invention provides articles implantable within the body, such as bone prostheses, that have an integral, as-cast macrotextured surface over at least a portion of the bone-engaging surface of the articles. The macrotextured surface formed on the implantable articles includes pores that have undercut edge profiles. Such surface features enable the implantable articles to have improved bone fixation mechanics. That is, once implanted in the body, the textured surface encourages the growth of hard tissue (i.e., bone) into the pores, thus forming a positive interlock between the implanted article and the new and existing bone tissue.

Figure 1:
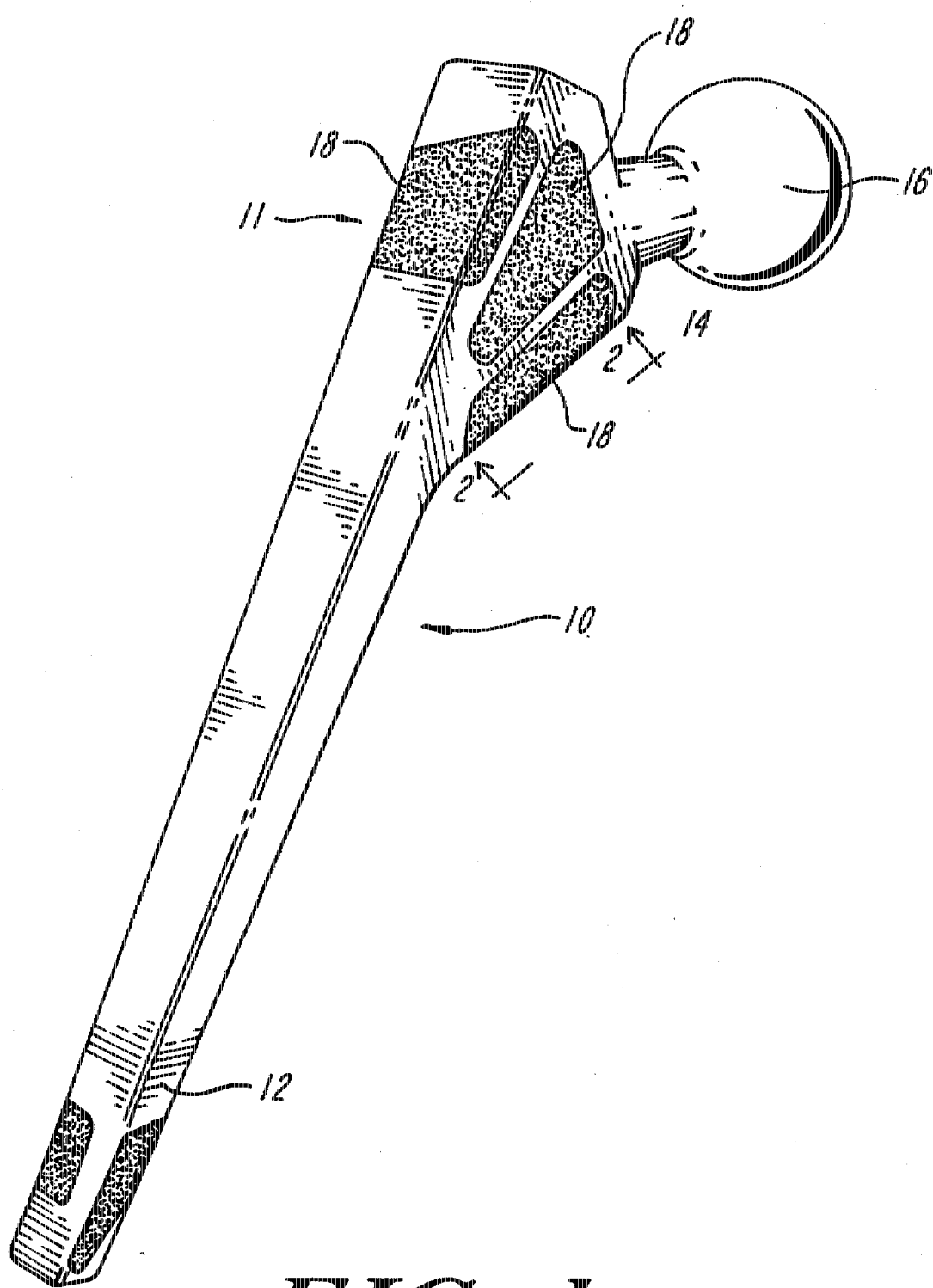
FIG. 1 is a perspective view of a hip femoral constructed according the present invention.

FIGS. 1 through 4 illustrate representative bone prostheses encompassed by the invention. FIG. 1 illustrates a hip femoral component 10 having an elongate shaft 12 at a distal end thereof, a neck region 14, and a femoral head 16 attached to the neck. A proximal portion 11 of the hip femoral component 10 includes macrotextured, porous surface areas 18.

Figure 3:
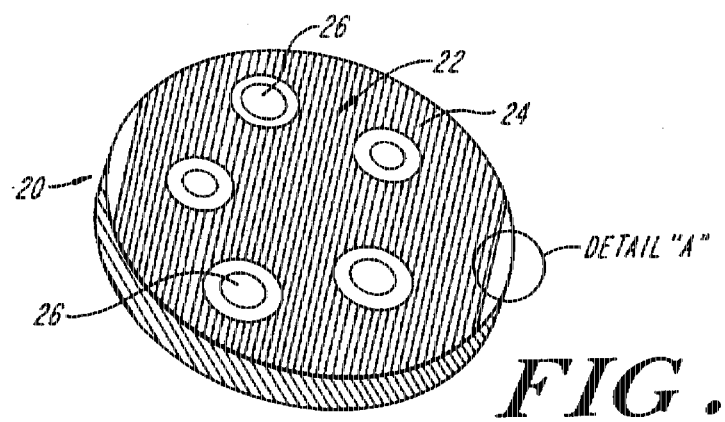
FIG. 3 is a perspective view of an acetabular shell constructed according to the present invention.

FIG. 3 illustrates another bone prosthesis in the form of an acetabular shell 20. Acetabular shell 20 includes an exterior bone-engaging surface 22, the entirety of which bears a macrotextured, porous surface 24. Bone-engaging surface 22 includes a plurality of holes 26 for seating bone screws (not shown).

Figure 2:
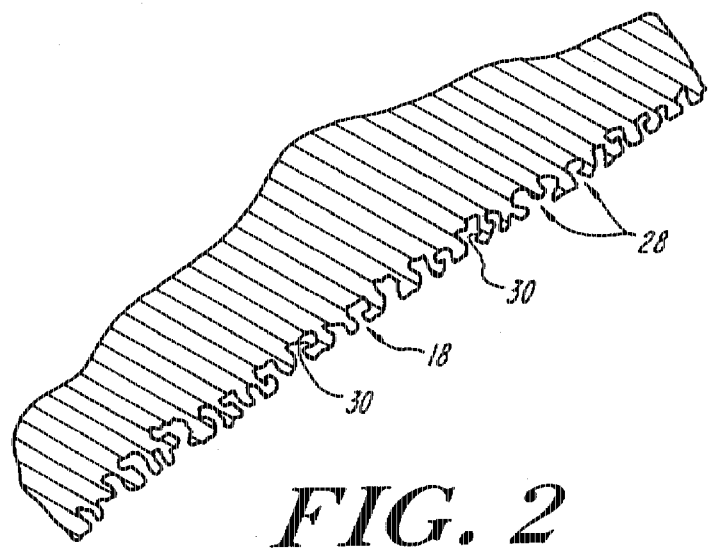
FIG. 2 is a section view, at section 2—2, of a textured surface region of the hip femoral of FIG. 1.
Figure 4:
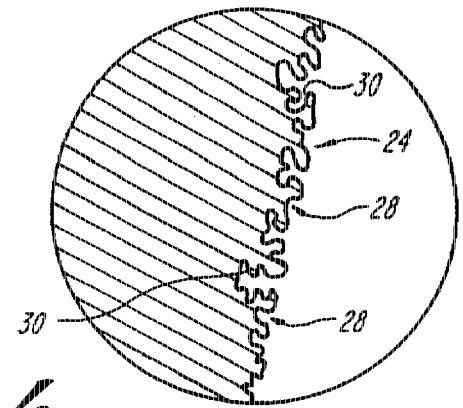
FIG. 4 is a detail view showing a textured surface region of the acetabular shell of FIG. 3.

FIGS. 2 and 4 illustrate detail views of macrotextured, porous surface regions 18, 24. Macrotextured, porous surface regions 18, 24 include pores 28, some of which have undercut edges 30.

Although not illustrated, other implantable bone prostheses may also include the integral, as-cast macrotextured bone-engaging surface regions disclosed herein. Additional prostheses include, but are not limited to, knee femorals, tibial plateaus, components of artificial elbow and shoulder joints, and spinal implants.

The implantable bone prostheses of the invention can be manufactured from a variety of biocompatible materials known to those having ordinary skill in the art. Exemplary materials include titanium, stainless steel, and cobalt-chromium alloy.

The term "macrotextured", as used herein, refers to a textured surface which includes surface features such as pores or voids that range in diameter from approximately 150 to 600 micrometers. This size range corresponds roughly to the particle size of a medium sand, on the fine end, and to a medium coarse sand and on the large end. The term "undercut edge profiles", as used herein, refers to the geometry of surface features of the macrotextured surface wherein the dimensions or profiles of the surface features are larger, at least in one direction, with increasing distance away from the level of the nominal surface of the prosthesis. Alternatively, this term refers to surface feature geometries in which horizontal cavities are formed in features that extend outward from the surface. This description should be qualified, however, in that the dimensions need not yield successively greater areas. Rather, it is only required that at the edge between a solid surface and an adjacent pore or void in 8 the solid surface extend over the void with increasing height, or that the solid surface lie above or overhang the void. Viewed from the perspective shown in FIGS. 2 and 4, such features would include file-like tooth protrusions with a negative rake angle, as well as other vertical protrusions having an inward slant or a horizontally-aimed indentation below the top of a wall of the surface.

As previously mentioned, the macrotextured surface of the prostheses is comprised of pores having an approximate "diameter" or feature size of between 150 and 600 micrometers. A preferred pore size for optimum hard tissue is between approximately 250 and 300 micrometers in diameter. The porosity is a measure of the percentage of total void region of the macrotextured surface as seen in a section parallel to the surface. A preferred range of porosity is approximately 30 to 60 percent. The undercuts of the pores preferably have a depth of from approximately ½ to 1½ millimeters. Thus, the pores are relatively deep invaginations in the surface profile, relative to their in-plane dimensions. The pores are preferably one to three times as deep as their total horizontal extent.

The implantable articles of the present invention, while not limited to a particular design, may include the hip femoral component 10 illustrated in FIG. 1 as well as the acetabular shell 20 illustrated in FIG. 3. A substantial portion of the outer surface of these prosthetic devices is comprised of bone-engaging surfaces that include macrotextured surface regions into which trabecular bone growth is promoted. The incorporation of the integral, as-cast macrotextured surface of the claimed invention in these regions is intended to provide improved fixation of these devices to the surrounding bone.

As indicated above, the depth-to-diameter ratio of the preferred surface pores achieved by the invention is relatively large; approximately unity to about four or five. In practice, the provision of a rough surface with deep relief allows bone debris created by wear or during the initial fitting of the prosthetic surface against adjacent bone to fall or to be packed into the pores, thus promoting bone ingrowth and creating a good environment for subsequent trabecular bone growth. Bone ingrowth helps to fix the device and also behaves as a good seal by preventing wear debris from migrating. The textured surface characteristics of the prosthesis also provide a relatively larger area of surface contact at the bone-engaging surface for load bearing and coupling to natural bone. In addition, by providing undercuts in the prosthesis, new bone growth dovetails where it joins the surface, providing good rigidity of coupling against tensile forces acting in three axes. All of these features are expected to enhance the strength and lifetime of an implanted prostheses.

As previously discussed, the direct creation of surface porosity on a bone prosthesis can cause numerous manufacturing problems. The prosthesis is typically made of a strong material, such as a cast metal, which is formed at a high temperature. Although these items can be formed by investment casting from a wax model, with subsequent destruction of the investment or casting mold, it appears to be virtually impossible to produce positive patterns of the prosthesis with the desired, complex surface typography.

This problem is overcome in accordance with one aspect of the present invention which provides a novel process for manufacturing implantable articles, such as bone prostheses, having the surface relief features described herein. In particular, the novel method for making an implantable bone prosthesis having an integral, as-cast macrotextured surface utilizes a stereolithographic process to prepare a positive model of a part to be cast. The positive model preferably is manufactured from a solid, heat destructible material such as a polymer. Using stereolithographic techniques, the positive model is formed from a liquid chemical that is selectively solidified by application, in desired areas, of reactive levels of energy. The energy is applied successively and at various points within a fluid reservoir of the reactive chemical, in a computer controlled pattern, to selectively solidify the reactive chemical in a series of layers as necessary to manufacture a solid three-dimensional object having a desired shape.

Techniques for stereolithographic manufacture of solid objects are disclosed in U.S. Pat. No. 4,929,402 (Hull), which is hereby incorporated by reference. Such a process can be adapted to prepare positive models of implantable bone prostheses having a bone-engaging surface, at least a portion of which is a macrotextured, porous region with undercut edge profiles. The resulting positive models can be used in casting processes to yield corresponding implantable bone prostheses having integral, as-cast macrotextured surfaces with undercut edge profiles and other complex textured features that are not obtainable through conventional casting processes.

The stereolithographic process of the invention involves providing a reservoir of a liquid, reactive chemical that is convertible to a heat destructible solid upon application of a sufficient level of reactive energy. Energy is focused within the reservoir of the reactive chemical at desired points or planes in a predetermined computer controlled pattern using computer aided design and computer aided manufacturing (CAD/CAM) techniques. The focusing of energy at desired locations within the reservoir causes solidification of the reactive chemical in the desired areas. Successive solidification of reactive chemical at adjacent points or planes within the fluid reservoir yields a solid, three dimensional object of a desired size and shape.

Figure 5:
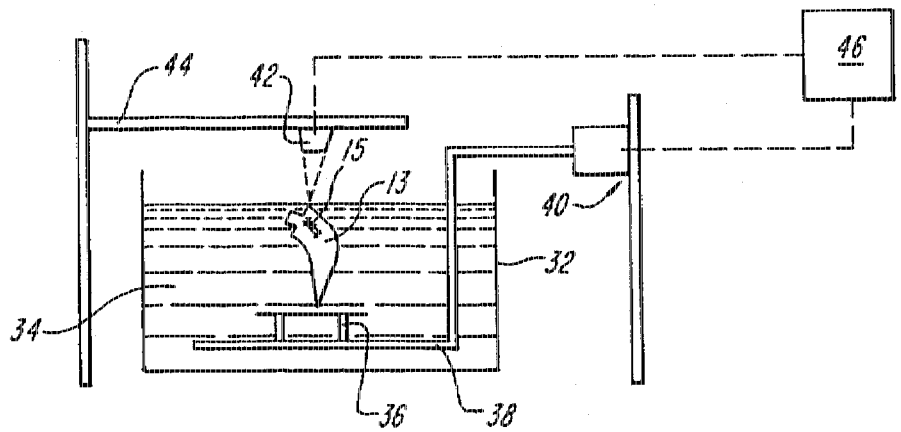
FIG. 5 illustrates the manufacture of a positive model of a hip femoral by a stereolithography process.

FIG. 5 schematically illustrates the application of a stereolithographic process to the manufacture of a positive model 13 of an implantable bone prosthesis in the form of a hip femoral that has a macrotextured surface region 15. A vessel 32 houses a reservoir of liquid reactive chemical 34. A stand 36 is disposed within the reservoir and is supported by a platten 38. Platten 38 is associated with a computer controllable elevator device 40 that facilitates vertical, Z axis movement of the platten 38 and stand 36. A computer controllable energy source 42 is mounted on an overhead support 44 and is able to be moved in the X and Y axes. A computer controller 46 communicates with elevator 40 and energy source 42 to control movement in the X, Y and Z directions and to control delivery of energy from the energy source 42.

Figure 6A:
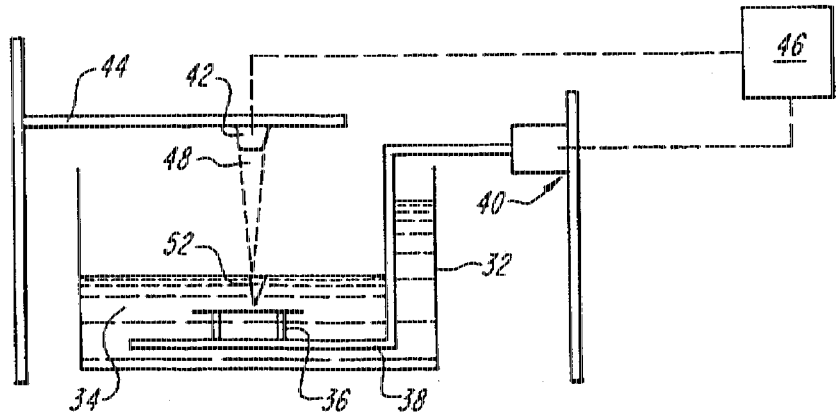
FIGS. 6A–6C sequentially illustrate the formation of a positive model of a hip femoral through a stereolithography process.
Figure 6B:
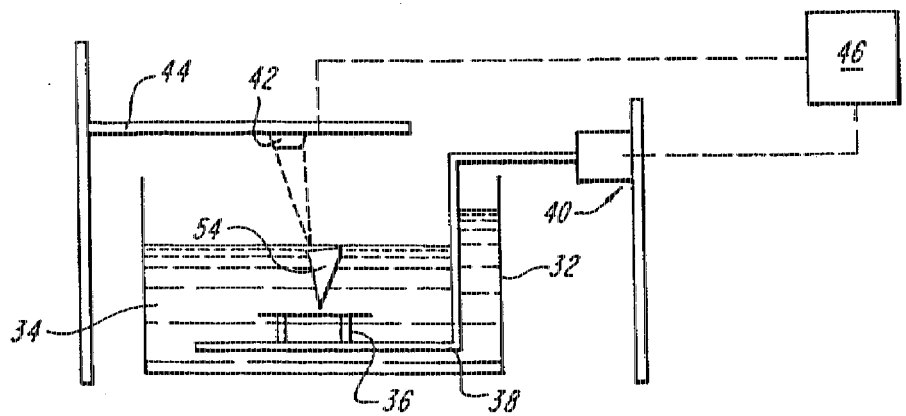
Figure 6C:
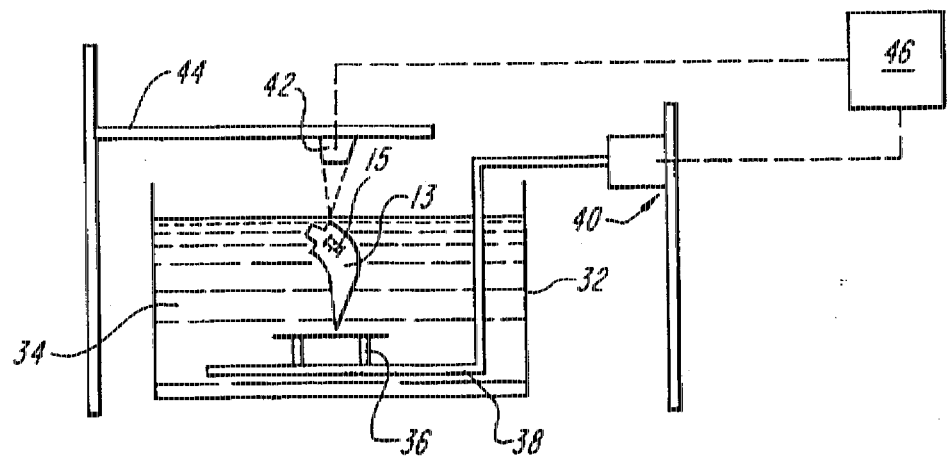

FIGS. 6A through 6C sequentially illustrate the stereolithographic manufacture of positive models for implantable bone prostheses according to the present invention. In FIG. 6A the stereolithographic process is initiated by focusing a beam of energy adjacent to the stand 36 within fluid reservoir 34 in a series of adjacent planes at a magnitude and for an amount of time necessary to solidify the reactive chemical. Distal portion 52 of hip femoral model 13 is formed after curing several adjacent layers of receive chemical. After the formation of each layer the elevator device 40 vertically moves stand 36 and platten 38 by a distance necessary to form the next layer. FIG. 6B illustrates the solidification of additional layers to form a further segment 54 of the model to be formed. This process is repeated, in a computer controlled sequence, to fully develop the hip femoral model 13 as illustrated in FIG. 6C. Alternatively, the energy source 42 can be sequentially focused at different levels within the fluid reservoir 34 necessary to form a subsequent solid layer without vertically moving stand 36 and platten 38.

Once the object, such as positive model 13, is fully formed the elevator device 40 can be raised to its maximize height and the object can be removed from the platform. Preferably, the object is then ultrasonically rinsed in a solvent, such as acetone, to dissolve the liquid, uncured reactive chemical while not affecting the cured solid object. Further curing of the object can then be effected by exposing it to additional ultraviolet energy. In one embodiment the object can be further cured by placing it under an intense ultraviolet light such as a 200 watt per inch UV cure lamp. Additional curing can also take place in a curing oven that utilizes UV lamps.

Stereolithography thus enables the manufacture of solid models of articles to be cast by successively curing thin layers of a reactive chemical. A programmed, moveable spot beam or plane of a reactive level of energy, focused on a surface or layer of the creative chemical, is used to form a solid cross section of the object at the surface of the liquid or at the interface of the focused beam and the liquid. After the formation of each layer the object (or the focal point of the energy beam) is moved, in a programmed manner, away from the liquid surface by the thickness of one layer, and the next cross section is then formed and adhered to the preceding layer that defines a portion of the object. This process is continued until the entire object is formed.

In another embodiment, the stereolithographic process of the invention can be used to form desired surface features on selected regions of implantable bone prostheses prepared by other processes, such as injection molding. According to this embodiment the previously formed implantable article can be placed on stand 36 within fluid containing vessel 32. Energy 48 can be focused at a desired surface region of the article, in a desired pattern, as necessary to build upon the existing surface of the model a desired surface texture 15. One requirement of this process is that the previously formed prosthesis be made of a material upon which the cured reactive chemical will adhere and which is heat destructible in its solid state. Once the desired surface texture is formed in the object, the object can be removed in the usual manner and ultrasonically rinsed with solvent and further cured.

Solid models prepared by the stereolithographic processes described above preferably have macrotextured bone-engaging surfaces as described above. The computer driven controller 46 can be programmed to manufacture solid models that incorporate desired surface texture features at selected regions of their bone-engaging surfaces. Various macrotextured surface patterns can be formed on the bone-engaging surfaces of the solid models, and FIGS. 7 and 8 illustrate representative patterns that can be formed.

Figure 7:
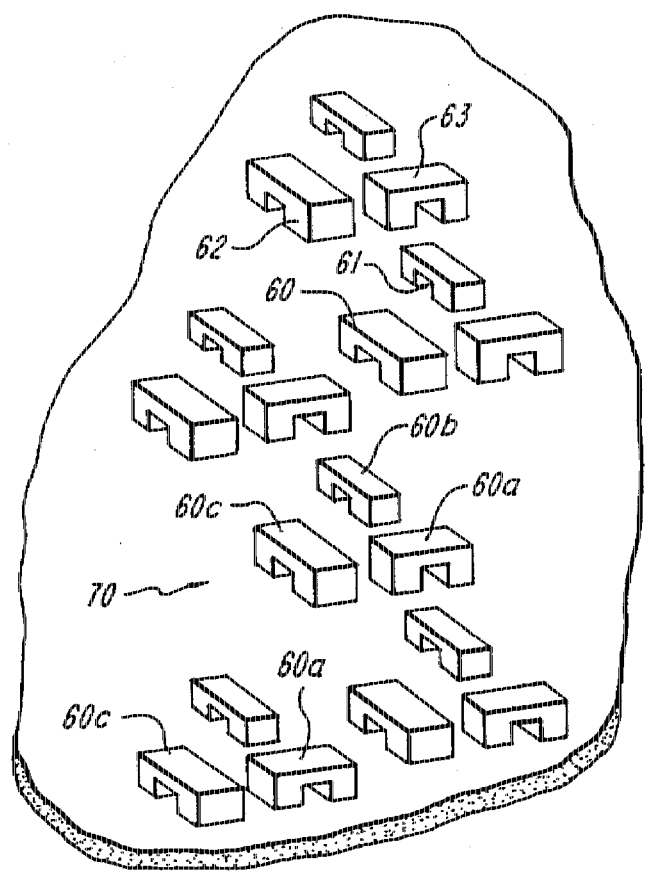
FIG. 7 is a detailed view of one simple undercut surface pattern made according to the present invention.

FIG. 7 shows an enlarged and simplified perspective view of one pattern 70 suitable for the macrotextured surface of the present invention. A plurality of bridges or arches 60 protrude above the nominal surface level of model 69. Each bridge 60 has legs 62, a top surface 63 and an underpass 61 that passes partially or completely through the surface. Preferably the bridges 60 are closely spaced and elongated in one of several different directions, as illustrated by the mutually orthogonal orientations of bridges 60a and 60b, or 60a and 60c. Other arrays of simple anchor structures are also possible, in which the bridges are arranged differently, or augmented or replaced by other shapes such as protruding hooks, undercut pits, ridges or the like.

Figures 8, 9:
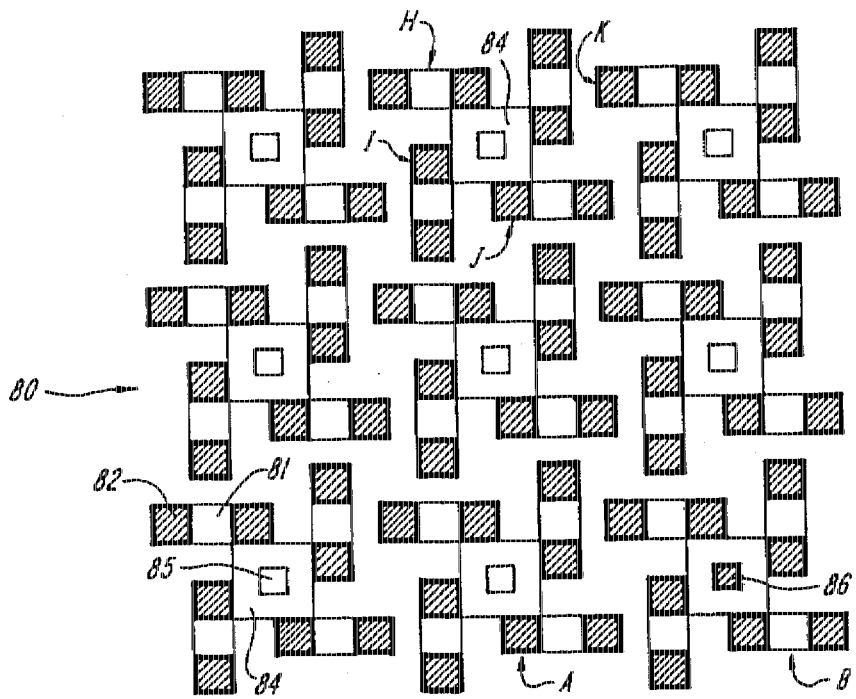
FIG. 8 is a detailed view of an array of undercut surface features forming a macrotextured surface according to the present invention.
FIG. 9 is a flow chart illustrating a sequence of steps used to manufacture implantable articles according to the present invention.

FIG. 8 illustrates a form of a presently preferred macrotextured pattern 80, wherein shaded squares 82 correspond to the legs 62 shown in FIG. 7, and the unshaded squares 81 between adjacent legs correspond to the undercuts 61 shown in FIG. 7. In this multiply-repeated pattern, four undercut bridges H, I, J, K are arranged, arm-like, about a central block region 84 which, as shown, is twice as wide as the leg 82, and that in turn has a central dimple 85 or peak 86 extending down or up, respectively, in its center. The shaded legs may, for example, be formed as three-dimensional layers of solidified reactive chemical using a stereolithography process with a height of six layers totaling about 0.61 mm. Preferably, the undercut 81 extends half that height, and the dimple 85 or post 86 is about 0.35 mm square and extends three layers down or up from the nominal center platform 84. Dimples 85 are illustratively half height, i.e., about 0.304 mm or three layers tall. The illustrated pattern has greatly interconnected topography, with the through holes or undercut tunnels 81 located to pass under the top surface of the bridge, and adjacent to the vertical face of the central block or platform 84. This surface topography promotes interlocked bone growth along several different planes.

Two illustrated variations of this pattern include variation A having a central dimple 85, and variation B having a central peak or post 86. These patterns may alternate, or the surface texture may comprise entirely one type of regular pattern. It will be noted that this artificial texture is readily susceptible to computerized generation, and may be numerically manipulated or embodied in a simple program to drive an energy source used in a stereolithography process so that the pattern is formed sideways or on a rising slanted surface such as the walls formed by minor horizontal variations in pattern contour in each layer of a vertical wall.

The reactive chemical useful with this process is one which can change from liquid state to solid state upon application of energy. An example of such a reactive chemical is a polymer that can be transformed to the solid state by sufficient levels of ultraviolet light or other forms of energy stimulation such as electron beams, visible or invisible light, reactive chemicals applied by ink jet or by a suitable mask.

Among the preferred reactive chemicals are those that are photocurable liquids and possess rapid curing properties when subjected to light sources. Exemplary photocurable chemicals are those that are curable by exposure to Ultraviolet (UV) light. Another requirement of suitable reactive chemicals is that they be somewhat adhesive so that successive layers of a model to be formed will adhere to one another. The viscosity of the reactive chemicals must be low enough so that additional reactive chemical will flow across the surface of the partially formed object upon movement of the elevator device. Preferably, the reactive chemical will absorb light (e.g., UV light) so that a reasonably thin layer of material is formed. The chemical should also be soluble in a suitable solvent in its liquid state while being insoluble in the same solvent in its solid state. This enables the object to be washed free of the reactive chemical once the object has been formed.

Useful reactive chemicals must also be heat destructible in their solid state. Preferred materials are those that melt or destruct at about 200°F. This heat-destructibility is essential as the objects formed through the stereolithographic process are positive models of articles to be cast. During the casting process the models are encased in a ceramic forming binder material and once the binder solidifies, heat is applied to melt and extract the models leaving behind cavities that represent negative images of the articles to be cast.

An exemplary reactive chemical useful with the present stereolithographic process is Potting Compound 363, a modified acrylate made by Locktite Corporation of Newington, Conn. A process useful to make a typical UV curable material is described in U.S. Pat. No. 4,100,141, which is hereby incorporated by reference.

Energy forms that can be used to transform the reactive chemical from the liquid to the solid states include thermal energy, ultraviolet radiation, impinging radiation, electron beam or other particle bombardment, and x-ray radiation. Ultraviolet light is among the preferred energy forms.

The energy source 42 for use in the stereolithographic process can be a cadmium laser that emits a UV light source. The laser preferably reflects off of variable angle mirrors (not shown), which are computer controlled to direct and focus the beam at a desired location. A preferred laser is a 40 milliwatt laser that emits a beam diameter of about 0.010 inch. The UV light source is useful in that it effects partial curing of the solid object being formed. Further curing of the object can be effected in a curing oven that utilizes UV lamps, as noted above.

FIG. 9 is a flow chart that illustrates an overall process of manufacturing cast articles according to the present invention. After forming a solid, heat destructible model of an article to be cast according to the present invention, either by manufacturing the model entirely by stereolithography or by forming only a macrotextured surface pattern on a previously formed model, the models are encased in a ceramic forming refractory material. This can be done by joining one or more of the models to a runner system, and then entirely encasing the runner system and joined models in the refractory material. Alternatively, a single model can be encased in a refractory material. Once the refractory material dries and hardens to form an investment assembly, the investment assembly is heated to a temperature and for a time period sufficient to melt or destroy the material from which the models are made. The molten material from which the model is made is then extracted from the investment assembly. The investment assembly can then be fired for a sufficient period of time to create a ceramic shell that includes one or more cavities that represent negative images of an article to be formed. Molten casting material, such as a metal or metal alloy, is then poured into the shell and is allowed to fill the cavities. When the metal cools a solid, cast article is formed. The shell can then be fractured by a variety of methods known in the art and the cast article can be removed.

The foregoing description of methods of manufacture and illustrative embodiments is presented to indicate the range of constructions to which the invention applies. Variations in the physical architecture and casting processes of the present invention will be readily apparent to those having ordinary skill in the art, and such variations are considered to be within the scope of the invention in which patent rights are asserted, as set forth in the claims appended hereto.

What is claimed is:

1. A process for casting an implantable article, comprising the steps of:

preparing one or more solid, heat destructible positive models of the implantable article, or portions thereof, by a stereolithography process involving providing a liquid material, curable to a heat destructible solid upon contact with stimulating energy, selectively directing to the liquid material a source of stimulating energy of sufficient intensity to cure the liquid material in a desired two dimensional pattern to form a solid surface, and continuously ensuring that the solid surface is fully coated with the liquid material and repeatedly directing the source of stimulating energy at desired locations, in a predetermined sequence, on or adjacent to the solid surface yielding successive layers of the solid surface that form a solid, three dimensional positive model of the implantable article to be cast, the positive models having on at least a portion of their exterior surfaces a macrotextured region including macropores having a diameter between about 150 and 600 microns wherein at least some macropores have undercut edge profiles;

assembling one or more of the positive models to a runner system to form a cluster assembly;

building a shell around the cluster assembly by applying one or more coatings of a refractory material to the cluster assembly while allowing the refractory material sufficient drying time between successive applications of refractory to form, upon drying, an investment assembly;

recovering the positive models from the investment assembly by heating the investment assembly to a temperature sufficient to melt or destroy the positive models such that the material from which the positive models are made can be extracted from the investment assembly leaving a shell having one or more cavities; and filling the shell with a molten casting material such that the molten casting material fills the cavities in the shell to form, upon cooling, solid implantable articles having on at least a portion of their exterior surfaces a macroporous textured surface including macropores wherein at least some of the macropores have undercut edge profiles.

2. The process of claim 1 further comprising, prior to the step of filling the shell, the step of preheating the shell at a temperature and for a duration sufficient to remove any residual material from which the positive models are made, and to add fired strength to the shell.

3. The process of claim 1 wherein the liquid material includes a photocurable polymer.

4. The process of claim 1 wherein the liquid material is an acrylate resin.

5. The process of claim 1 wherein the stimulating energy is selected from the group consisting of thermal energy, electromagnetic energy, an electron beam, a beam of high energy particles, ultraviolet light, visible light, a laser beam.

6. The process of claim 1 wherein the casting material is a metal or metal alloy.

7. A process for manufacturing an implantable article, comprising the steps of:

preparing by a stereolithography technique one or more solid, heat destructible positive models of the implantable article, or portions thereof, each positive model having on at least a portion of its exterior surface a macrotextured surface including macropores having a diameter between about 150 and 600 microns wherein at least some macropores have undercut edge profiles;

assembling one or more of the positive models to a runner system to form a cluster assembly;

building a shell around the cluster assembly by applying one or more coatings of a refractory material to the cluster assembly while allowing sufficient drying time for the refractory material between successive applications of refractory to form an investment assembly;

recovering the positive models from the investment assembly by heating the investment assembly to a temperature sufficient to melt or destroy the positive models such that the material from which the positive models are made can be extracted from the investment assembly leaving a shell having one or more cavities;

firing the shell at a desired temperature and for a sufficient duration to add fired strength to the shell; and filling the shell with a molten metal or metal alloy such that the molten metal or metal alloy fills the cavities in the shell to form, upon cooling, metal or metal alloy implantable articles having on at least a portion of their exterior surfaces a macroporous textured surface including macropores with undercut edge profiles.

8. A process for manufacturing an implantable article, comprising the steps of:

preparing one or more heat destructible positive models of the implantable article;

forming on at least a portion of the exterior surface of the positive models, by a stereolithography technique, a macrotextured surface including macropores having a diameter between about; 150 and 600 microns wherein at least some macropores have undercut edge profiles, the macrotextured surface being comprised of a heat destructible solid material;

assembling one or more of the positive models to a runner system to form a cluster assembly;

building a shell around the cluster assembly by applying one or more coatings of a refractory material to the cluster assembly while allowing sufficient drying time for the refractory material between successive applications of refractory to form an investment assembly;

recovering the positive models from the investment assembly by heating the investment assembly to a temperature sufficient to melt or destroy the positive models such that the material from which the positive models are made can be extracted from the investment assembly leaving a shell having one or more cavities;

firing the shell at a desired temperature and for a sufficient duration to add fired strength to the shell; and filling the shell with a molten metal or metal alloy such that the molten metal or metal alloy fills the cavities in the shell to form, upon cooling, metal or metal alloy implantable articles having on at least a portion of their exterior surfaces a macroporous textured surface including macropores with undercut edge profiles.

\* \* \* \* \*